United States Patent [19]

Kozulic

[11] Patent Number: 6,017,436
[45] Date of Patent: Jan. 25, 2000

[54] COMB FOR FORMING SAMPLE WELLS, WITH ENLARGED LOADING AREAS, IN ELECTROPHORESIS GELS

[75] Inventor: Branko Kozulic, Zurich, Switzerland

[73] Assignee: Guest Elchrom Scientific AG, Cham, Switzerland

[21] Appl. No.: 09/099,062

[22] Filed: Jun. 16, 1998

Related U.S. Application Data

[62] Division of application No. 08/775,028, Dec. 23, 1996, Pat. No. 5,800,691.

[51] Int. Cl.[7] .......................... G01N 27/26; G01N 27/447
[52] U.S. Cl. .......................... 204/620; 204/606; 204/616
[58] Field of Search ..................... 204/620, 621, 204/619, 616, 606, 470, 466, 456

[56] References Cited

U.S. PATENT DOCUMENTS

| | | | |
|---|---|---|---|
| 4,431,506 | 2/1984 | Gorman, Jr. et al. | 204/619 |
| 4,795,541 | 1/1989 | Hurd et al. | 204/620 |
| 5,073,246 | 12/1991 | Chu et al. | 204/619 |
| 5,284,565 | 2/1994 | Chu et al. | 204/619 |
| 5,318,682 | 6/1994 | Singer | 204/620 X |
| 5,407,552 | 4/1995 | Lebacq | 204/619 |
| 5,512,146 | 4/1996 | Brunk et al. | 204/620 X |
| 5,514,255 | 5/1996 | Gautsch et al. | 204/620 X |
| 5,618,399 | 4/1997 | Gautsch et al. | 264/620 |
| 5,627,022 | 5/1997 | Renfrew et al. | 204/619 X |

FOREIGN PATENT DOCUMENTS

| | | | |
|---|---|---|---|
| 134622 | 3/1985 | European Pat. Off. | 204/616 |

*Primary Examiner*—Jill Warden
*Assistant Examiner*—John S. Starsiak, Jr.
*Attorney, Agent, or Firm*—Lowe Hauptman Gopstein Gilman & Berner

[57] ABSTRACT

A gel for electrophoresis in a horizontal mode which contains at least one sample well with an enlarged loading area that is formed in an elevated gel segment. At least a front wall of the sample well consists of a substantially vertical part and a non-vertical part, where the non-vertical part is declined at an angle sufficiently steep that the sample loaded on the non-vertical part slides down into the sample well. Any sample molecules that during electrophoresis enter the gel through the non vertical part of the front wall migrate only through the elevated gel segment. They also exit this segment, so that substantially no double bands, which could complicate the interpretation of experimental results, are detected.

1 Claim, 7 Drawing Sheets

COMB FOR FORMING SAMPLE WELLS, WITH ENLARGED LOADING AREAS, IN ELECTROPHORESIS GELS

This application is a division of application Ser. No. 08/775,028 filed Dec. 23, 1996, now U.S. Pat. No. 5,800,691.

This invention is directed to a novel structure for the gel used in submerged gel electrophoresis. It more particularly refers to such gel structures which enable more accurate and efficient substantially simultaneous introduction of a plurality of samples into a plurality of sample wells

BACKGROUND OF THE INVENTION

In gel electrophoresis, a mixture of molecules present in a sample is resolved into its components either partially or completely by differential migration of the components in a gel. The gel can be run positioned vertically or horizontally, and in both formats the samples are usually loaded into sample wells. It is also possible to load the samples directly on a gel surface when that surface is exposed to air, that is, when the gel is run horizontally in a flat-bed mode. Loading the samples directly on the gel surface is not possible in submerged gel electrophoresis, which is known also as submarine electrophoresis, because the sample molecules would spread into the surrounding electrophoresis buffer.

The sample wells are typically formed by means of a comb, which is generally a rectangular piece 5 to 20 cm long, from 0.2 to 3 mm thick and a few centimeters high, and which has numerous protrusions separated by spaces. The comb, also known as sample well-former, is positioned in its place before relation takes place. Following relation the comb is removed, leaving cavities that are of complimentary size and shape. A top view of a gel with 12 sample wells is shown in FIG. 1A. A side view of a similar gel is shown in FIG. 1B. Electrophoresis migration occurs from left to right, as in all other figures below showing similar side views. This design is typical for majority of gels that are currently used for DNA analysis in the submerged gel electrophoresis mode. Prior to loading, a sample solution is mixed with another solution characterized by a high density, commonly known as loading buffer. Since the resulting density of the sample is higher than the density of the running buffer, the sample sinks to the bottom of the well when released from a pipette positioned above the well. In FIG. 1 the loading area is equal to the sample well area, defined by the length and width of the well. If a sample is released anywhere outside that area, it will not enter the sample well.

Modifications of sample wells, and corresponding well-forming devices, are known in the prior art. Thus, U.S. Pat. No. 5,318,682 by Singer describes combs having protrusions of trapezoid shape, which produce sample wells that are wider at the top than at the bottom. This design allows closer spacing of sample wells, and thus makes possible the analysis of a larger number of samples than is possible with rectangular protrusions. Another modification is described in U.S. Pat. No. 4,795,541 by Hard et al. With that modification, a large sample volume can be applied even to very thin gels.

Sample wells of novel design for vertical gels have been disclosed in U.S. Pat. No. 5,304,292 by Jacob et al. Known are also devices that circumvent the use of sample wells. For example, U.S. Pat. No. 5,464,515 by Bellow discloses a device which contains a porous material able to absorb sample molecules prior to loading the samples onto a gel. The absorbed molecules migrate from the porous material to the gel in the electric field. Another way of loading multiple samples simultaneously is disclosed in PCT WO 95/20155 Patent Application by Williams.

The modifications described above have been worked out in order to address specific limitations, or improve certain features, of the manner in which samples are loaded to electrophoresis gels. The ease of sample loading becomes an important issue when many samples have to be processed. Gels with 50 and 100 sample wells are available from Guest Elchrom Scientific under the name Wide Mini S-50 and Wide Mini S-100 gels. These gels were developed for high-throughput applications, and their wells are positioned in 25-well rows. Samples are best applied with a 12-channel pipette, such that alternate wells are filled with one pipetting stroke. Experience has shown that some operators are not always able to deliver all 12 samples precisely to corresponding sample wells without spills into adjacent wells or onto the gel surface. Positioning of 12 pipette tips precisely over 12 alternating wells requires that the operator has steady hands. Even then a problem arises when any one of the 12 pipette tips is not perfectly straight.

Another type of spill is related to PCR samples that have been overlaid with oil. To withdraw a portion of the sample for analysis, the pipette tip needs to pass through an oil layer. Traces of oil then always remain in the sample. Very often this oil does not allow smooth displacement of the sample from the pipette tip into the well. Sometimes the oil causes formation of a "sample bubble" at the pipette tip, which, after bursting, disperses the sample over a wide area.

Yet another source of spills exists during loading of samples onto the gels that are run in submarine mode at a high temperature, for example at 55° C. A part of the sample is often prematurely ejected due to expansion of the air inside the pipette tip after the tip has been placed in the warm running buffer. Regardless of the cause of spills, when molecules from the spilled sample enter the gel, they are subsequently detected as additional bands. Such bands complicate evaluation of the band pattern, and if not recognized, may lead to incorrect interpretation of the experimental results.

One evident way to make sample loading easier is to increase the width and/or length of the wells. However, this approach is associated with serious drawbacks. Thus, the larger the sample wells are, the smaller is the number of samples that can be run on a given gel, making the cost of analysis higher. Moreover, if a multichannel pipette is to be used for sample loading, then sample wells must be spaced according to the spaces which exist between pipette tips. The tips are 9 mm apart in standard multichannel pipettes, so that the distance between the middle of each two adjacent wells must be either 9 mm, for filling each well, or 4.5 mm, for filling alternate wells with one pipetting stroke. Two adjacent wells are usually spaced 1 to 2 mm apart. These dimensions impose a strict limit on the choice of possible lengths of sample wells. On the other hand, increasing the width of sample wells is associated with worsening of resolution. The resolution is related to the width of separated bands, and sharp bands are possible only when molecules enter the gel in a narrow starting zone. In the absence of a stacking gel and a discontinuous buffer system, typical for submerged gel electrophoresis, a narrow starting zone will be achieved only if mobilities of the sample molecules are greatly reduced as they enter the gel. For small molecules, and for low solids content gels, the difference between free mobility and the mobility in a gel is small. Therefore, the width of the starting zone is directly related to the width of the sample well. Consequently, the resolution will be worse in a gel with wide sample wells than in a gel with narrow sample wells, keeping all other parameters constant. In the practice, a compromise is found between band sharpness, the volume that can be loaded into a sample well, and the ease of sample loading.

It has now been found that sample loading can be made easier by a new design of sample wells. With the new design the loading area is enlarged without concomitant increase of the length or width of the sample well. The modification is particularly suitable for gels that are run in the submerged gel electrophoresis mode. The novel design is especially advantageous when loading samples with a multichannel pipette.

OBJECTIVES OF THE INVENTION

It is an objective of the present invention to provide a gel containing sample wells with enlarged loading area.

Another objective is the provision of a comb of such a shape that it produces sample wells having an extended loading area.

It is a further objective of the present invention to provide a gel casting cassette which possesses a comb that produces sample wells with an extended loading area.

It is also an objective of the present invention to provide an improved method of gel electrophoresis, where the improvement is related to easier sample loading and fewer problems due to sample spills, particularly during loading.

Other objectives will become more apparent when the present specification is read in conjunction with appended figures.

BRIEF DESCRIPTION OF THE INVENTION

In accord with an fulfilling these objects, one aspect of this invention resides in a gel having a novel sample well design which is particularly well suited to use where a plurality of samples wells are intended to be filled substantially simultaneously. This is of particular value for employment in submerged gel electrophoresis. The novel sample well design of this invention provides an additional segment of gel above the nominal height of gel conventionally used for submerged gel electrophoresis. In the conventional gel structure, the sample wells have opposite walls that are generally parallel to each other. The conventional walls of sample wells are substantially completely vertical. In accord with this invention, the additional gel segment added above the conventional height of the gel has at least an upper part of its front wall that is disposed at an angle, of less than 90°, with respect to the substantially vertical lower front wall part. The angle of this upper part of at least the front wall is such that sample that is initially deposited on it will slide down and lodge in the area where the front wall is substantially vertical. However, if the sample well is overfilled, or if any portion of the sample remains in the vicinity of the upper, non-vertical, part of the front wall, it will migrate only through the additional upper gel segment and will not interfere with the separation of the bands relative to the portion of the sample in the bottom of the sample well.

DETAILED DESCRIPTION OF PREFERRED EMBODIMENTS

Figure 1A:
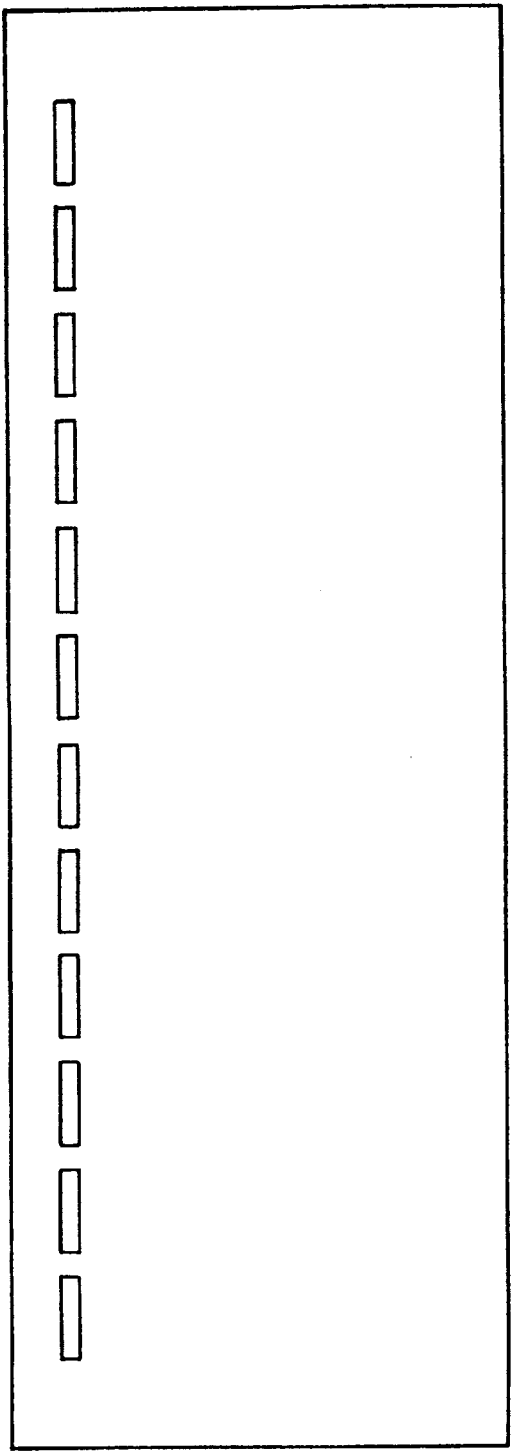
FIG. 1A is a top view of a gel with sample wells having a design that is common in the prior art.
Figure 1B:
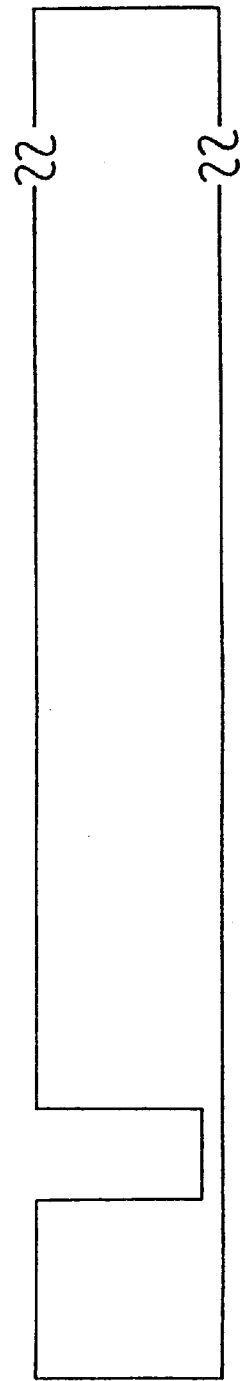
FIG. 1B is a side view of a sample well that is characteristic of prior art designs.
Figure 2A:
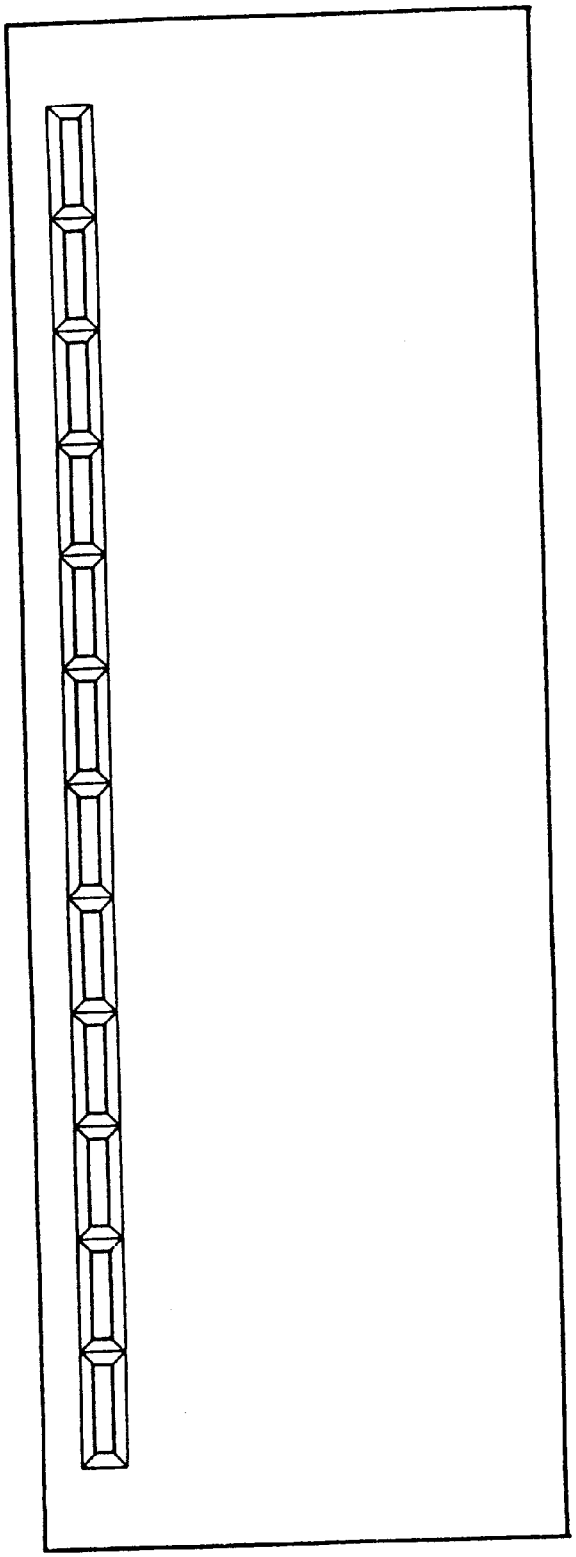
FIG. 2A shows a top view of a gel according to one aspect of this invention with sample wells of enlarged loading areas.
Figure 2B:
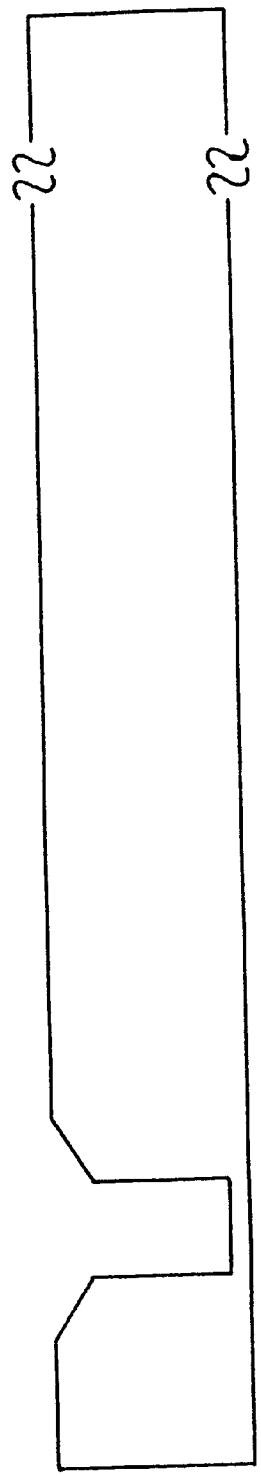
FIG. 2B is a side view of the gel of FIG. 2A.

One possibility of having a gel with an increased loading area, without increasing the width of the sample zone, is shown in FIG. 2A (top view) and FIG. 2B (side view). The upper part of the front and rear walls of the sample well are slanted, so that the sample loading area is larger. The sample which is pipetted over the slanted area will slide down into the well due to its high density. Sample loading is thus easier. This design, however, is associated with several drawbacks. First, the useful volume of the sample that can be placed in the well is reduced, and is equal to the vertical part of the front wall of the well. Second, filling the well to a level above the vertical portion will result in double bands after recording from above, because sample molecules entering the gel through the slanted portion will migrate ahead of the molecules entering the gel through the vertical portion. Third, even without overfilling, if after loading any sample remains on the slanted area, a weak band may be visible in front of a major one. Due to these drawbacks, the well configuration shown in FIG. 2A and FIG. 2B cannot be considered as an improvement over the configuration shown in FIGS. 1A and 1B.

Figure 3A:
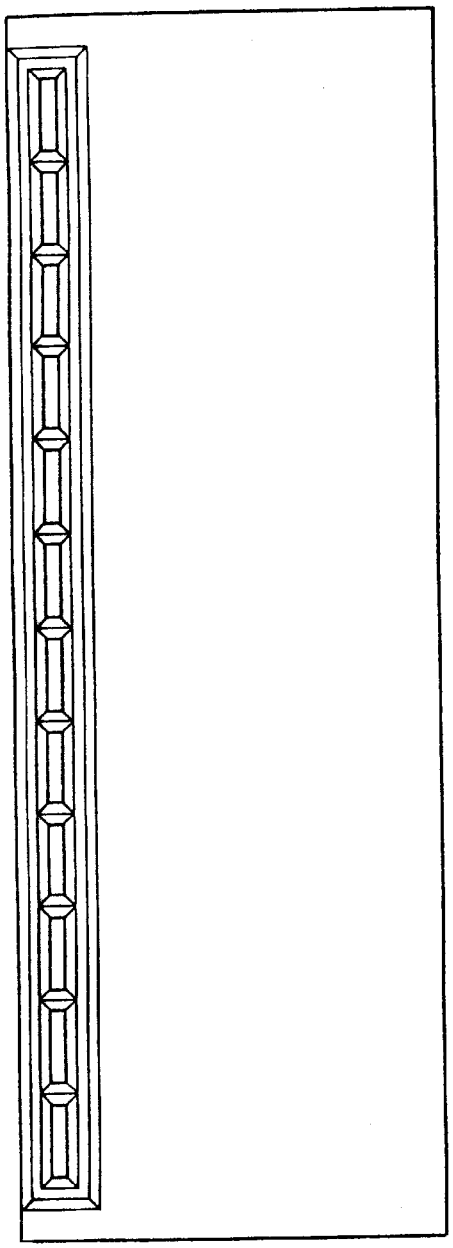
FIG. 3A depicts a top view of a gel according to another aspect of this invention containing wells with enlarged loading areas formed on an elevated gel segment.
Figure 3B:
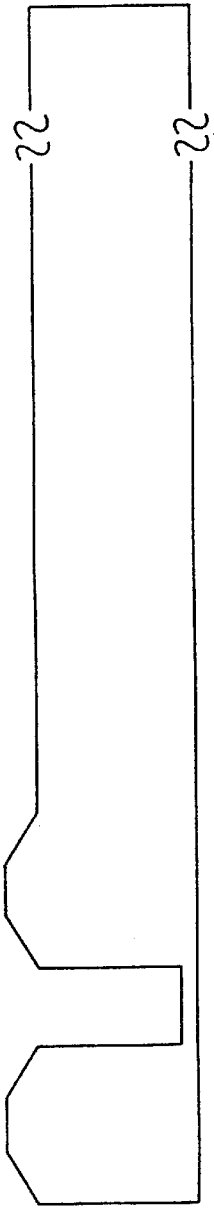
FIG. 3B is a side view of the sample well with enlarged loading area of FIG. 3A.
Figure 3C:
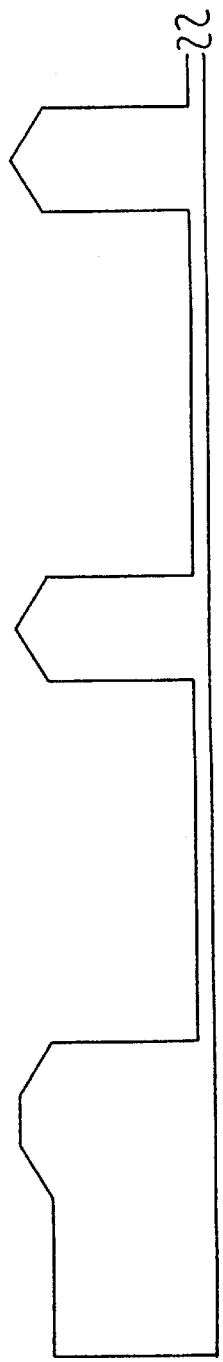
FIG. 3C is another side view of the sample wells of FIG. 3A with enlarged loading areas.

A new design which does not suffer from the above drawbacks is shown in FIG. 3A (top view), FIG. 3B (side view), and FIG. 3C (another side view). In this configuration of sample wells, the gel part with an enlarged loading area is elevated in relation to the rest of the gel. As can be seen from FIG. 3B, the vertical portion of the sample well is now equal to the desired gel thickness. Therefore, there is no reduction in the useful volume that can be loaded into the sample well. The vertical part of the front wall could be extended upwards, but that would not increase the useful volume of the well. In the case of overfilling, when the sample level reaches the slanted portion of the sample well, there will be no double bands. Those molecules which enter the gel from the slanted area of the front wall will migrate only through the elevated part of the gel, and will exit at the opposite slanted side. The same will happen with any sample molecules that may accidentally remain on or in the vicinity of the slanted area after loading the well.

Figure 4A:
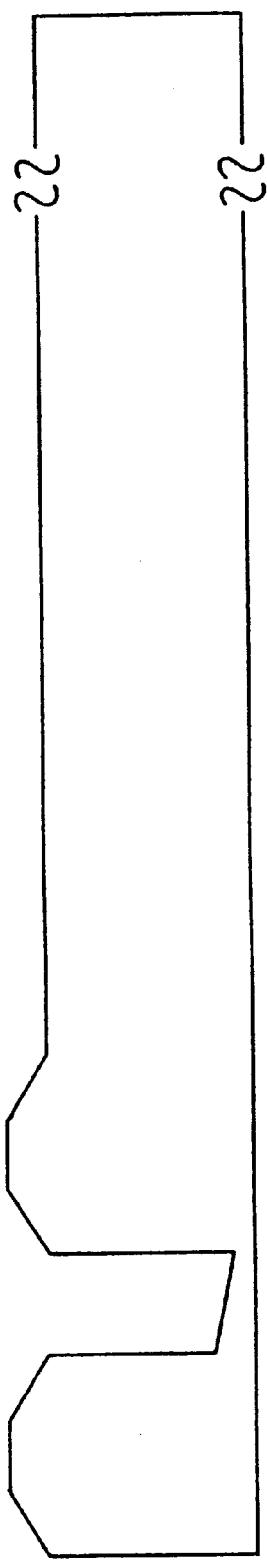
FIG. 4A is a side view of another sample well, according to another aspect of this invention, with enlarged loading areas and having a slanted bottom.

A modification of the well design is shown in FIG. 4A, where the bottom of the well is slanted such that the back vertical side becomes shorter. The preferable value for the angle β (FIG. 4B) is from 2° to 30°, more preferable from 5° to 15°, and the optimal value is about 10°. The advantages of the wells with slanted bottoms include easier removal of the comb, better entry of sample molecules, and better stability of the gel layer between the gel support and the sample well. In other modifications, sample wells can occupy a larger or a smaller portion of the gel thickness compared to the portion shown on the presented figures. The bottom of the well can be also curved, but the curved bottom must terminate higher on the rear side than on the front, so that molecules being analysed enter the gel only through the front wall and not through the curved part of the bottom. While it is preferable to have at least a part of the front and rear walls of the well vertical, that is not necessary as long as any declination from vertical still allows removal of the comb after gelation.

Gels used for submerged gel electrophoresis are usually 3 to 5 mm thick, but thinner or thicker gels can be used as well. A larger sample volume can be applied to a thicker gel, but more gel material is needed for its preparation. Furthermore, the staining-destaining process takes more time and background staining is stronger with thicker gels. These facts must be considered when choosing an appropriate gel thickness. As mentioned above, the width of the sample well can be varied, but in most cases it will be from 0.5 to 3 mm, preferentially from 0.8 to 1.5 mm on typical gels that are from 4 cm to 20 cm long. On shorter gels, it may be advantageous to have wells of a smaller width. When the gel is 3 mm thick and the sample well 1.5 mm wide, then the ratio between the gel thickness and the sample well width is 2. This relative proportion is displayed in FIGS. 1–4. When the angle of the slanted area α is 30° (FIG. 4B), then the height d of the elevated part of the gel which forms the extended loading area (FIG. 4B) is 0.6 mm. That is only a 20% increase in the gel thickness. The width of the loading area has increased 1 mm on each side, so that it is now 3.5 mm. That represents 230% larger width over which the sample can be released, making sample loading easier, which is the primary object of this invention.

Figure 4B:
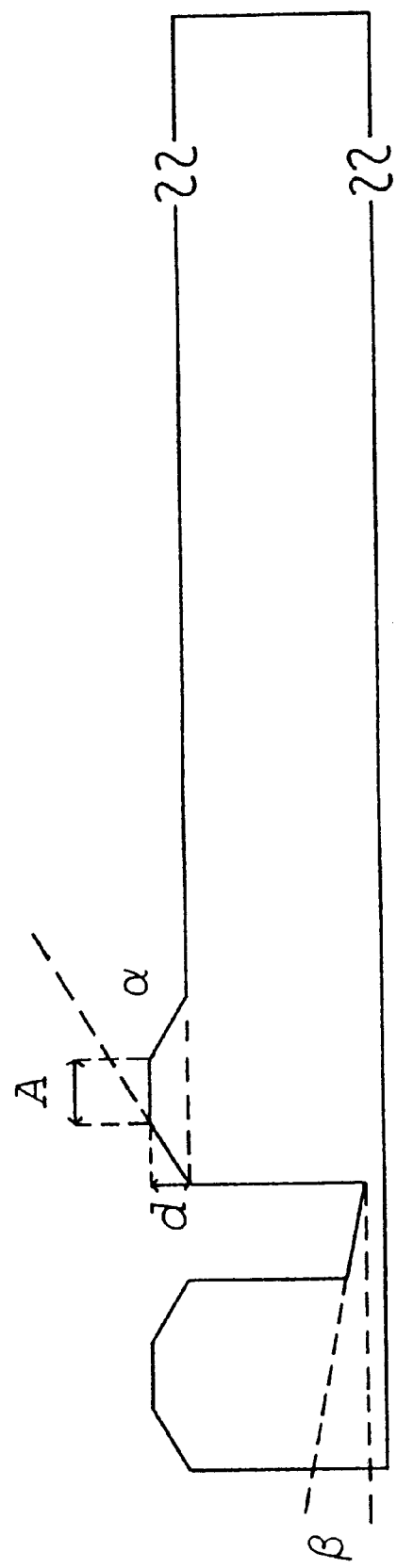
FIG. 4B shows the same well together with designation of various distances and angles discussed in the instant specification.

Various values can be chosen for the angle α (FIG. 4B). It is important that the angle is sufficiently steep so that the sample released on the slanted area slides down into the sample well. On the other hand, the steeper the angle, the larger is the height d of the elevated gel part for a given enlargement of the loading width. The height d should not be large, because then more gel material would be needed for casting the gel, and the elevated gel portion may cause problems in blotting. Blotting refers to the process by which the separated molecules are transferred from a gel to a membrane placed in direct contact with gel surface. Any unevenness of the gel surface may cause problems due to poor contact with the membrane, or due to uneven pressure when the membrane is placed on the other side of the gel which is pressed into a blotting cassette. Based on the above considerations, suitable values for the angle α are from about 10° to 60°, and the optimal values are between about 15° and 45°. An angle α of 30° is shown in FIGS. 4A and 4B.

In FIG. 4B, the width A of the flat part of the elevated gel segment can vary, taking account of the considerations already put forward. In fact, the length can be zero, so that the elevated portion ends with a sharp peak. That design is less desirable owing to less favourable mechanical stability, which is especially important for packaging and transportation of precast gels.

In FIG. 3C, the elevated portion between sample wells has a height that is equal to the height of the elevated portion in the front and the rear of the sample wells. The elevated part ends with a peak (FIG. 3C). Further, the angle of the slanted surfaces between sample wells is equal to an angle of 30°. It should be noted that this angle can be chosen different from α, and that there is no requirement that the angle cannot be 90°. With vertical extension between sample wells, however, the loading area would not be extended at the well length.

Figure 5A:
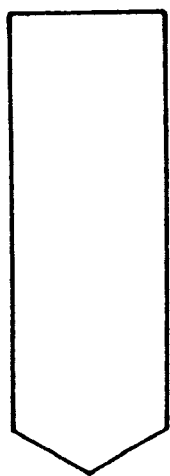
FIG. 5A is a schematic representation of a drill used for enlarging a top portion of a comb to form the desired elevated gel portions between sample wells of the shape shown in FIG. 3C.
Figure 5B:
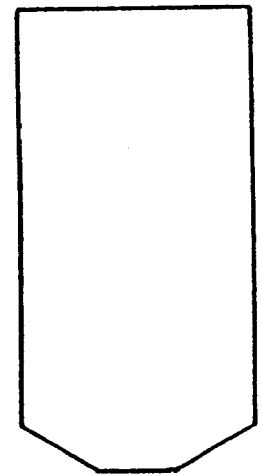
FIG. 5B is a schematic representation of a drill used for enlarging a top portion of a comb to form the desired elevated gel portions at the rear and at the front of the sample wells, and also on the left side of the first and on the right of the last well as depicted in FIG. 3A and 3B.

One advantage of the design shown in FIGS. 3 and 4 is that manufacturing of the complimentary combs is possible by precision drilling. Only two drills, schematically shown in FIG. 5, are necessary. The drill shown in FIG. 5A is used to form the elevated portion between sample wells. The drill of FIG. 5B is used to create the elevated gel portion in the front and at the rear of the sample wells, and also on the left and on the right of the first and the last well, respectively. The manufacturing is done by conventional methods, and the drills can be made of metal or diamond.

Figure 6:
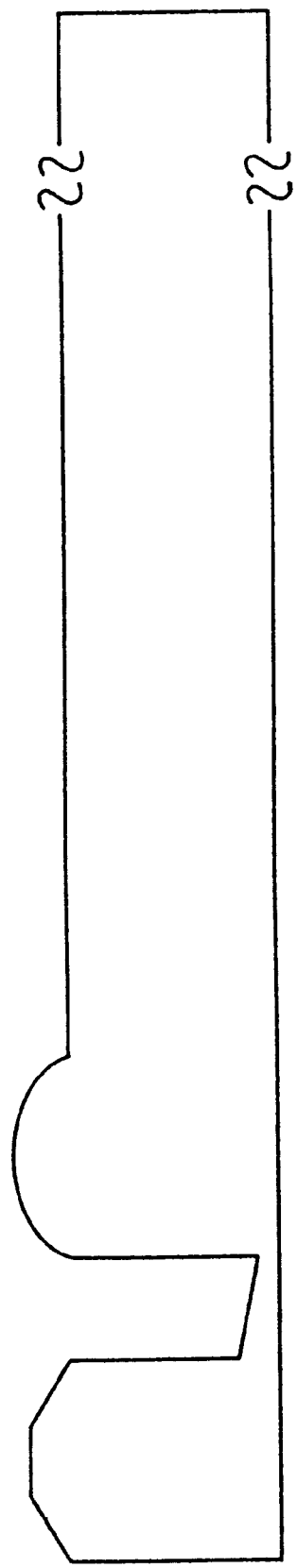
FIG. 6 is side view of a gel according to another aspect of this invention, with a sample well having an enlarged loading area, in which a front part of the elevated gel segment is curved.

The elevated gel portion does not have to contain sharp edges. A desired enlargement of the loading area can be formed also with curved gel surface, such as shown in FIG. 6. This, or a similar, configuration may be preferable when the combs are produced by a manufacturing method other than drilling, such as injection moulding. The combination of injection moulding and precision drilling may be preferred in some cases. Other modifications are also possible. For example, the front and the rear slanted surfaces may have different heights or shapes, as shown in FIG. 6. Moreover, the elevated part at the rear of the sample well can be omitted. That would reduce the enlarged loading area by one half, but some other advantages mentioned above would remain. Furthermore, the elevated portion of the gel can be positioned differently from the position depicted on FIG. 3A It can extend up to the end of the left and right gel sides, and it does not need to start at the edge of the rear end of the gel, as shown in FIG. 3B.

Figure 7A:
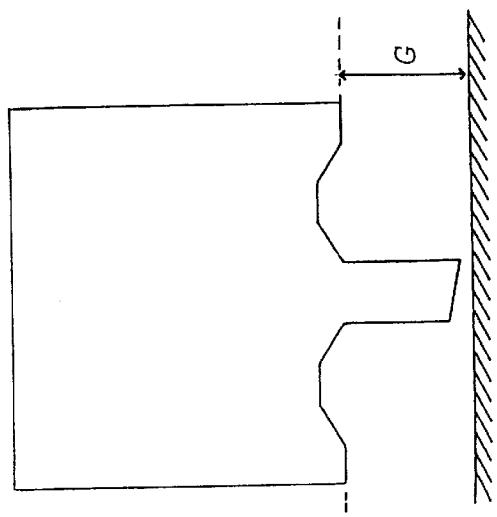
FIG. 7A is a schematic side view of a comb that can be placed into a casting frame to form sample wells of enlarged loading area as described in the specification.

The gels containing sample wells of the present invention can be formed in a cassette with the comb representing an integral, non-removable part of the cassette. The cassette may also have walls that determine the thickness of the gel. Alternatively, the devices which determine the thickness and overall size of the gel may be physically separated, or separable, from the comb. In practice, the combs are usually made of plastic, but other materials that do not interfere with gel formation can also be used. Suitable plastic materials include, but are not limited to, plexiglass (polymethyl methacrylate), delrin (polyformaldehyde), and teflon (polytetrafluoroethylene). A schematic side view of a removable comb is shown in FIG. 7A. The shape and size of the comb are fully complimentary to the shape and size of the sample well of FIG. 3. Conventional means to fix the comb at desired gel height are not shown. The comb may contain means that improve its smooth removal from the gel. For example, positioning two screws vertically, one at the right and the other at the left end of the comb, and turning them against a base on which the comb rests, affects smooth lifting of the comb.

Figure 7B:
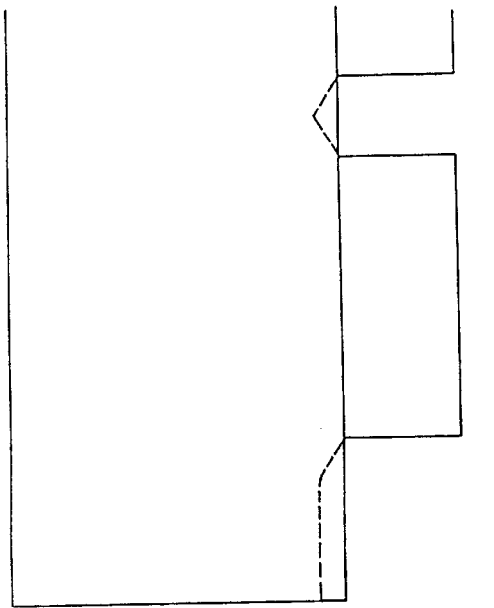
FIG. 7B is a schematic side view of the left end of the comb of FIG. 7A.
Figure 7C:
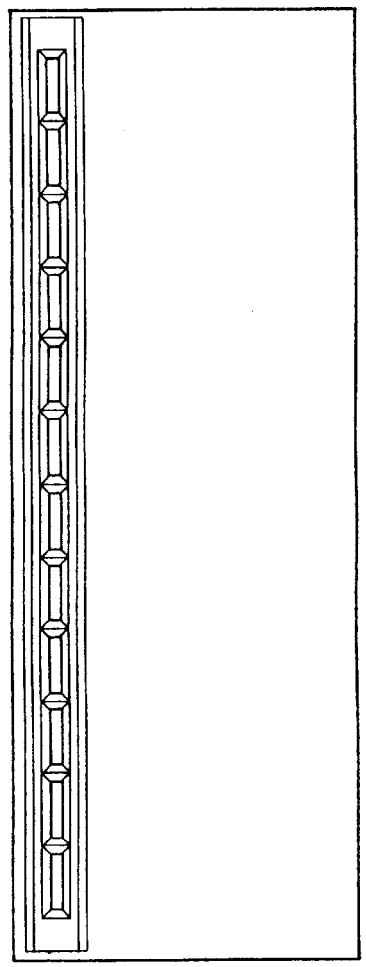
FIG. 7C is a top view of a gel, according to another aspect of this invention, containing sample wells with enlarged loading areas formed by a removable comb of the design shown in FIGS. 7A and 7B.

Another side view of a portion of the comb is displayed in FIG. 7B. With a comb of this design, the elevated gel part will have a different form from that shown in FIG. 3A on the left of the first well, and also on the right of the last well, as shown in FIG. 7C. This change allows for better escape of the air during pouring of the gel solution. For the same reason, it is advantageous to keep the casting tray slightly tilted during pouring, and then place it flat for relation. The volume of the solution should be such that its level comes approximately to the height G (FIG. 7A). In practice, the level will often be slightly higher or lower when agarose gels are cast, due to evaporation of water from the warm gel solution. During relation the upper gel surface may be covered to prevent evaporation or contact with the air. This surface may contain other elevations or depressions if desired, but in most cases the only elevation will be the one used to create the wells with enlarged loading area.

The number of wells that are formed with a comb of present invention can vary from one, for preparative work, to any other number that is required for a particular application. The gel size is not restricted in any way. The present design is most beneficial for the gels that are run in the submerged mode, but sample wells of the present configuration can also be formed on the gels that are used for flat-bed, not submerged, electrophoresis, which are also run horizontally.

The gels presently in use for electrophoresis can be prepared by different processes, including polymerization, temperature-induced relation, and chemical cross-linking simultaneous with relation. The sample wells with enlarged loading area described herein can be formed from any suitable gel, regardless of the process by which the relation takes place.

EXAMPLE OF THE PRACTICE OF THE INVENTION

Example 1

Preparation of a gel having sample wells with enlarged loading area, and use of such a gel in electrophoresis.

Using two drills of the shape shown in FIG. 5, a comb with thirteen protrusions was drilled in one part of a moulded plastic cassette. The length of each sample well was 7.5 mm, the width 1.5 mm, and the height about 2.6 mm, with bottom of the well slanted by about 10 degrees as shown in FIG. 4A. The volume of the sample that can be filled in the vertical part of the sample well is thus about 30 $\mu$l neglecting a slight distortion of the well following comb removal. The gel was prepared in the cassette by cross-linking 1% agarose with 1,4-butanediol diglycidylether, as described in U.S. Pat. No. 5,371,208. Following removal of the cross-linking reaction byproducts and equilibration against 30 mM TAE buffer, the gel was equilibrated with 0.5 $\mu$g/ml ethidium bromide in the same buffer. Identical amounts of a DNA marker (1 kb ladder, Life Technologies) was loaded in different final volumes, including 5 $\mu$l, 10 $\mu$l, 15 $\mu$l, 20 $\mu$l, 25 $\mu$l, 30 $\mu$l, 35 $\mu$l, 40 $\mu$l, 45 $\mu$l and 50 $\mu$l. With the last two volumes, spilling of the sample was observed on all sides of corresponding sample wells, indicating that sample volume was more than sufficient for filling the vertical and the slanted part of the wells. The gel was run in the TAE-EtBr buffer at 10 V/cm for 25 min at 20° C. in Elchrom's SEA 2000 apparatus. Following photography, no difference in the sharpness of bands could be observed between the lanes, and no double bands were visible. This result indicates that DNA molecules which entered the gel through the slanted part of the front wall have migrated out at the other side of the elevated gel segment.

The present invention is considered to be most beneficial;y used in connection with submerged gel electrophoresis, which is used to analyse different types of molecules. They most frequently include biological macromolecules, in particular nucleic acids. However, proteins and other macromolecules can also be more easily loaded onto gels having sample wells of the configuration described in this invention.

It is to be understood that the invention is not limited to the illustrations described and shown herein, which are deemed to be merely illustrative of the best modes of carrying out the invention, and which are susceptible of modification of form, size and details of operation. The invention is rather intended to encompass all such modifications which are within its spirit and scope as defined by the claims.

What is claimed is:

1. A comb for use in producing a gel slab, containing at least one sample well adapted to receive sample molecules therein and from which said sample molecules can be caused to migrate through the gel by horizontal mode electrophoresis, wherein said sample well is produced in said gel by bringing said comb into association with a gellable composition, gelling said composition while in association with said comb, and then removing said comb whereby forming said gel slab containing said sample well;

wherein said gel slab comnprises a substantially flat top surface and additional gel material extending away from said top surface around the intersection of said sample well and said top surface, wherein said surrounding additional gel material defines an open extension of said sample well, said open extension having a cross sectional area, measured parallel to said top surface at a point where said additional gel material is furthest from said top surface, that is larger than a cross section area of said sample well;

wherein said comb comprises:
a main body including a surface that is generally planar,
a tine, comprising two portion, projecting substantially normal from said main body wherein a distal portion of said tine is adapted to form said sample well and a proximal portion of said tine is adapted to from said open extension of said sample well in said gels; and
at least one recess in said main body adjacent to said proximal portion of said tine;

wherein said proximal portion of said tine has a cross sectional area that increases from the intersection of said distal and proximal portions of said tine toward said main body;

wherein said intersection of said proximal and distal portions of said tine is substantially within a plane defined by said surface;

wherein said proximal portion of said tine includes at least one obtuse wall that forms an obtuse angle with a wall of said distal portion, and wherein said recess is bounded by at least said plane and said obtuse wall and is disposed away from said distal portion of said tine.

* * * * *